(12) United States Patent
Hayashi et al.

(10) Patent No.: US 8,133,513 B2
(45) Date of Patent: Mar. 13, 2012

(54) SOLID PREPARATION HAVING IMPROVED SOLUBILITY

(75) Inventors: Takashi Hayashi, Hyogo (JP); Asako Takakura, Hyogo (JP)

(73) Assignee: Shionogi & Co., Ltd., Osaka (JP)

( * ) Notice: Subject to any disclaimer, the term of this patent is extended or adjusted under 35 U.S.C. 154(b) by 373 days.

(21) Appl. No.: 12/294,036

(22) PCT Filed: Mar. 20, 2007

(86) PCT No.: PCT/JP2007/055624
§ 371 (c)(1),
(2), (4) Date: Oct. 22, 2008

(87) PCT Pub. No.: WO2007/108463
PCT Pub. Date: Sep. 27, 2007

(65) Prior Publication Data
US 2009/0105312 A1  Apr. 23, 2009

(30) Foreign Application Priority Data

Mar. 23, 2006 (JP) ................................ 2006-080778

(51) Int. Cl.
*A61K 9/14* (2006.01)
*A61P 31/455* (2006.01)
*A61P 43/00* (2006.01)

(52) U.S. Cl. ........................................ 424/488; 514/356
(58) Field of Classification Search .................. None
See application file for complete search history.

(56) References Cited

U.S. PATENT DOCUMENTS 4,412,986 A    11/1983  Kawata et al.
2007/0259050 A1*  11/2007  Blume et al. .................. 424/537

FOREIGN PATENT DOCUMENTS

| EP | 0 852 140 A1 | 8/1998 |
|---|---|---|
| EP | 1 356 807 A2 | 10/2003 |
| EP | 1 356 807 A3 | 1/2004 |
| JP | 09-309834 | 12/1997 |
| JP | 02-529519 A | 9/2002 |
| WO | WO-97/06781 A1 | 2/1997 |
| WO | WO-97/34610 | 9/1997 |
| WO | WO-00/29025 | 5/2000 |

OTHER PUBLICATIONS

Suzuki et al. "Influence of Water-Soluble Polymers on the Dissolution of Nifedipine Solid Dispersions Combined with Carriers". Chem. Pharm. Bull. 46(3) 482-487 (1998).*

Suzuki, H. et al., "Influence of Water-Soluble Polymers on the Dissolution of Nifedipine Solid Dispersions with Combined Carriers," Chem. Pharm. Bull. 46(3) 482-487 (1998).

Human Science Researches on Drug Discovery, etc. for the Year 2005, Prioritized Study Report.

* cited by examiner

*Primary Examiner* — Robert A Wax
*Assistant Examiner* — Danah Al-Awadi
(74) *Attorney, Agent, or Firm* — Birch, Stewart, Kolasch & Birch, LLP

(57) ABSTRACT

A preparation which can improve the dissolution property of a poorly water soluble drug even when the drug is contained in the preparation at a high content is provided.

When an addition amount of nicotinic acid amide and/or urea is 0.1 to 10% by weight in a solid preparation containing a poorly water soluble drug, and a water-soluble polymer, even a poorly water soluble drug, particularly a drug having a high content can be dissolved out from the preparation by an almost all amount.

13 Claims, 2 Drawing Sheets

[Fig.1]
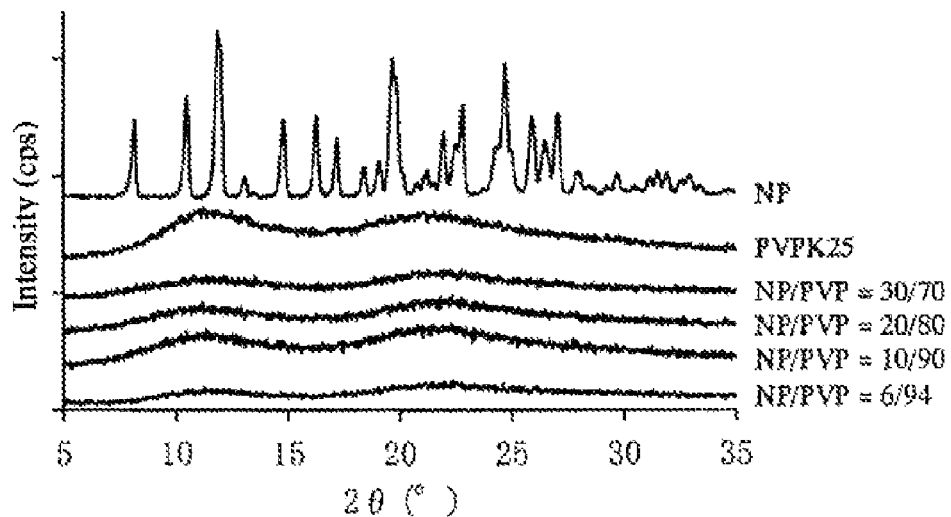
[Fig.2]
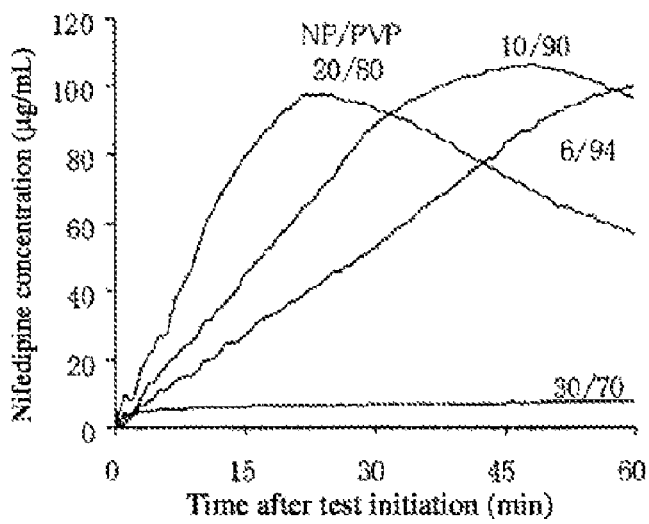
[Fig.3]
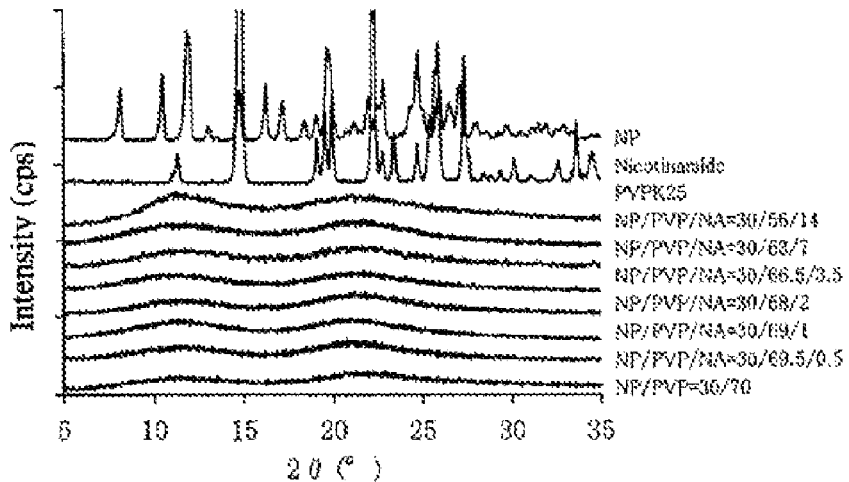

[Fig.4]
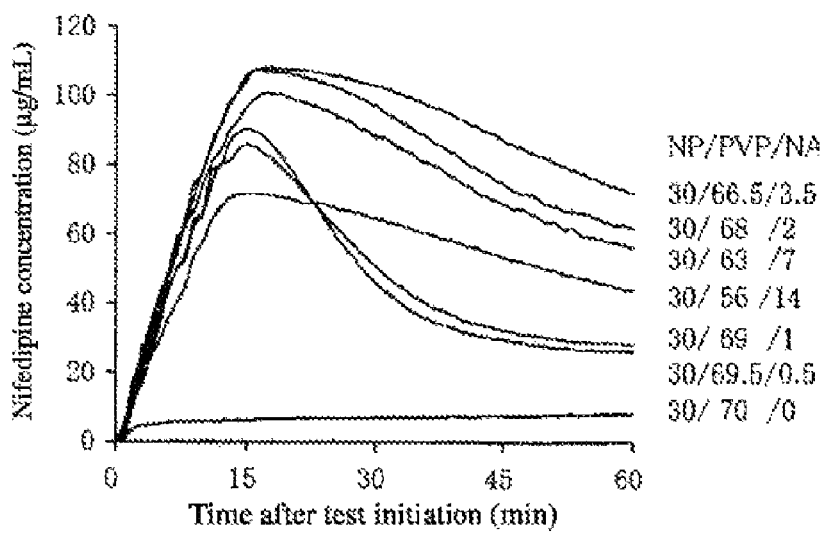
[Fig.5]
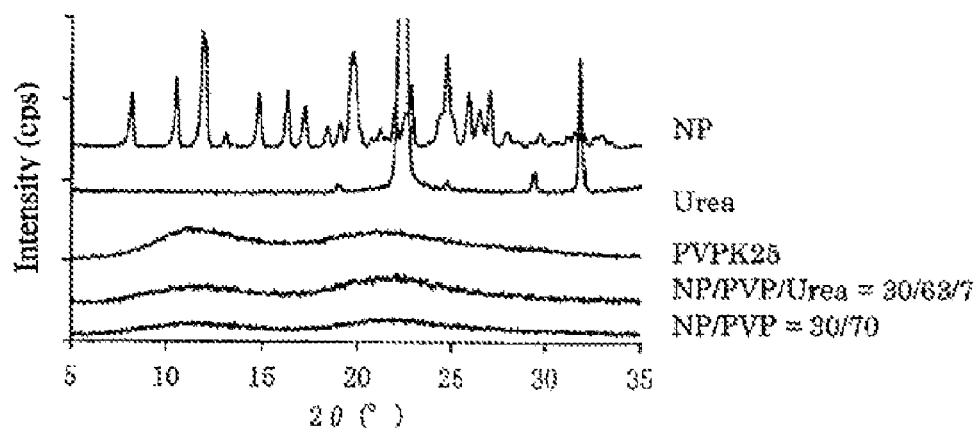
[Fig.6]
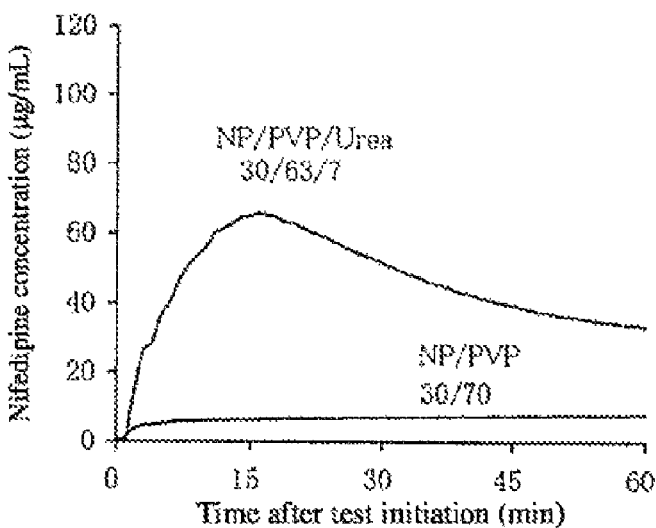

SOLID PREPARATION HAVING IMPROVED SOLUBILITY

This Application is the National Phase Under 35 U.S.C. §371 of PCT International Application No. PCT/JP2007/055624 which has an International filing date of Mar. 20, 2007, which claims priority to JP 2006-080778 filed on Mar. 23, 2006.

TECHNICAL FIELD

The present invention relates to a solid preparation containing a drug and a water-soluble polymer, comprising 0.1 to 10% by weight of nicotinic acid amide and/or urea, preferably 2 to 7% by weight of nicotinic acid amide and/or urea, for improving solubility of the drug.

BACKGROUND OF THE TECHNIQUE

An absorption amount of a poorly water soluble drug is small in many cases since the drug is not sufficiently dissolved in a digestive tract when orally administered. In such drug, an absorption ratio of the drug is decreased with the increase of administration amount, and the absorption ratio varies more easily due to digestion activity at fed state (mechanical stimulation due to constriction movement of digestive tract, increase in secretion amount of digestive fluid, prolongation of digestive tract retention time etc.) as compared with at fast state, the expected therapeutic effect is not obtained, or accidental adverse event is caused in some cases. For this reason, particularly, it is important for developing an oral preparation to enhance solubility of the drug from the solid preparation.

As one of means to improve solubility of the poorly water soluble drug in an aqueous liquid from the solid preparation, a solid dispersion in which a drug molecule is uniformly dispersed in inactive ingredients in the solid state is used.

A preparation containing nifedipine which is a poorly water soluble drug as such the solid dispersion, hydroxypropylmethylcellulose and polyvinylpyrrolidone as a water-soluble polymer, and 60% by weight of nicotinic acid amide as an additive is disclosed (Non-Patent Literature 1).

As a method of producing the solid dispersion, a process comprising heating or mechanochemically treating a preparation containing nicardipine hydrochloride, hydroxypropylmethylcellulose and 15% by weight of urea is disclosed (Patent Literature 1). Like this, nicotinic acid amide and urea are known as an additive for forming the solid dispersion.

However, in Non-Patent Literature 1, even when the water-soluble polymer is changed, the poorly water soluble drug has been dissolved out only by about a half amount at maximum. The process of Patent Literature 1 is a process of giving an excessive stress for the drug such as heating at a high temperature and mechanochemical treatment of the preparation. Therefore, any technique is not sufficient for the preparation of the solid dispersion. In addition, when a content of the drug in the preparation is high, solubilizing effect of the solid dispersion is reduced.

Non-Patent Literature 1: Chem. Pharm. Bull., vol. 46, 482-487, 1998

Patent Literature 1: International Publication Pamphlet WO 97/06781

DISCLOSURE OF THE INVENTION

Problems to be Solved by the Invention

The present inventor intensively studied, and found out that, when a water-soluble polymer and an amount of nicotinic acid amide or urea are contained in a preparation, solubility of the drug can be improved even at a high content of the drug.

Means to Solve the Problems

The present invention is mainly characterized in that, in a solid preparation containing a drug and a water-soluble polymer, when an additional amount of nicotinic acid amide and/or urea in the preparation is optimized, solubility of the drug can be improved. More particularly, in the solid preparation, when an additional amount of nicotinic acid amide and/or urea is 0.1 to 10% by weight, preferably, an almost all amount of the drug can be dissolved out from the preparation even at a high content of the drug, particularly a poorly water soluble drug. In addition, since nicotinic acid amide and urea are a neutral compound, they are expected to exhibit the dissolution promoting effect regardless of the pH dissolution property of the poorly water soluble drug and the pH state in the digestive tract. That is, the present invention related to the following invention.

(1) A solid preparation containing a drug and a water-soluble polymer, comprising 0.1 to 10% by weight of nicotinic acid amide and/or urea.

(2) The solid preparation according to (1), wherein a content of nicotinic acid amide and/or urea is 2 to 7% by weight.

(3) The solid preparation according to (1) or (2), wherein a content of the drug is 20 to 50% by weight.

(4) The solid preparation according to any of (1) to (3), wherein solubility in water of the drug is not more than 100 µg/mL.

(5) The solid preparation according to any of (1) to (4), wherein the water-soluble polymer is one or more selected from the group consisting of polyvinylpyrrolidone, water-soluble cellulose, polyvinyl alcohol, polyvinyl acetate, gelatin, agar, sodium alginate, pectin, pullulan, gum xanthan, gum arabic, chondroitin sulfate, hyaluronic acid and carrageenan.

(6) The solid preparation according to (5), wherein the water-soluble cellulose is one or more selected from the group consisting of hydroxypropylcellulose, hydroxypropylmethylcellulose, hydroxypropylmethylcellulose phthalate, hydroxypropylmethylcellulose acetate succinate and carboxymethylcellulose sodium.

(7) The solid preparation according to (5), wherein the water-soluble polymer is polyvinylpyrrolidone and/or hydroxypropylmethylcellulose acetate succinate.

(8) A method for improving solubility of a drug characterized in that 0.1 to 10% by weight of nicotinic acid amide and/or urea are contained in a solid preparation containing a drug and a water-soluble polymer.

Effect of the Invention

In the solid preparation of the present invention, an almost all amount of a drug, particularly a poorly water soluble drug can be dissolved out from the solid preparation by containing 0.1 to 10% by weight, preferably 1 to 8% by weight, more preferably 2 to 7% by weight of nicotinic acid amide and/or urea in the preparation.

BRIEF DESCRIPTION OF THE DRAWINGS

FIG. 1 An X-ray diffractogram of preparations having different contents of nifedipine (NP: nifedipine, PVP: polyvinylpyrrolidone).

FIG. 2 Nifedipine dissolution profile of preparations having different contents of nifedipine (NP: nifedipine, PVP: polyvinylpyrrolidone).

FIG. 3 An X-ray diffractogram of preparations having different contents of nicotinic acid amide (NP: nifedipine, PVP: polyvinylpyrrolidone, NA: nicotinic acid amide).

FIG. 4 Nifedipine dissolution profile of preparations having different contents of nicotinic acid amide (NP: nifedipine, PVP: polyvinylpyrrolidone, NP: nicotinic acid amide).

FIG. 5 An X-ray diffractogram of preparations having different contents of urea (NP: nifedipine, PVP: polyvinylpyrrolidone, Urea: urea).

FIG. 6 Nifedipine dissolution profile of preparations having different contents of urea (NP: nifedipine, PVP: polyvinylpyrrolidone, Urea: urea)

BEST MODE FOR CARRYING OUT THE INVENTION

Nicotinic acid amide used in the present invention may be nicotinic acid amide used in the medical field, and nicotinic acid amide listed in Japanese Pharmacopoeia, 14 Revision is preferable.

Urea used in the present invention may be urea used in the medical field, and urea listed in Japanese Pharmacopoeia, 14 Revision is preferable.

A content of nicotinic acid amide or urea in the preparation may be a content at which solubility of the drug can be improved, and is preferably 0.1 to 10% by weight, more preferably 1 to 8% by weight, further preferably 2 to 7% by weight. Nicotinic acid amide and urea may be used together and, when they are used together, an amount of a total of them may be in a range of the content. When an amount is less than this amount, there is a possibility that solubility of the drug can not be increased and, when an amount is more than this amount, there is a fear that solubility of the drug is decreased, and, since the crystal precipitation suppressing effect of the water-soluble polymer during a production process is decreased, the drug becomes easy to be crystallized upon removal of a solvent, and there is a high possibility that it becomes difficult to obtain an amorphous preparation.

As the drug to be applied in the present preparation, any drug can be used, and the drug is not particularly limited as far as it is a drug which can be orally administered, but is preferably a so-called poorly water soluble drug having low solubility in water. Herein, solubility in water of the drug refers to solubility of the drug at 37° C. in a buffer having a pH considerable as the environment in a digestive tract in a range of 1 to 8, and water, representatively, any of Japanese Pharmacopoeia Disintegration Test Solution First Solution, Disintegration Test Solution Second Solution, and water. Examples of the drug include compounds having solubility in water of 100 µg/mL or lower, further 50 µg/mL or lower, further 10 µg/mL or lower.

As the drug, specifically, one kind or two kinds or more of ingredients selected from a nutritional fortification health supplement, a pyretolytic analgesic antiphlogistic drug, a psychoactive drug, an anti-anxiety drug, an anti-depression drug, a hypnogenetic sedating drug, an anticonvulsant, a central nerve acting drug, a brain metabolism improving agent, a brain circulation improving agent, an anti-antiepileptic agent, a sympathetic analeptic agent, a gastrointestinal agent, an anti-ulcer agent, antitussive expectorant drug, an antiemetic agent, an anapnoic agent, a bronchodilator, a drug for allergy, a dental oral drug, an anti-histamine agent, a cardiotonic agent, an agent for arrhythmia, a diuretic drug, a hypotensive agent, a vasoconstrictive drug, a coronary vasodilator, a peripheral vasodilator, an agent for hyperlipemia, a cholagogue, an antibiotic, a chemotherapeutic, an agent for diabetes, an agent for osteoporosis, an antirheumatic drug, a skeletal muscle relaxant, anticonvulsive agent, a hormone agent, an alkaloid narcotic, a sulfa agent, a gout treating drug, a blood coagulation arresting agent, an anti-malignant tumor agent, and an anti-obesity drug are used.

Examples of the nutritional fortification health supplement include vitamins such as vitamin A, vitamin D, vitamin E (d-a-tocopherol acetate). Examples of the pyretolytic analgesic antiphlogistic drug include aspirin, acetaminophen, ethenzamide, ibuprofen, noscapine, serrapeptase, lysozyme chloride, tolufenamic acid, mefenamic acid, diclofenac sodium, flufenamic acid, salicylamide, aminopyrine, ketoprofen, indometacin, bucolome, and pentazocine.

Examples of the psychoactive drug include chlorpromazine, and reserpine. Examples of the anti-anxiety drug include alprazolam, chlordiazepoxide, and diazepam. Examples of the anti-depression drug include imipramine. Examples of the hypnogenetic sedating drug include estazoram, and perlapine. Examples of the central nerve acting drug include citicoline. Examples of the brain circulation improving agent include vinpocetine. Examples of the anti-antiepileptic agent include phenytoin, and carbamazepine. Examples of the gastrointestinal agent include scopolia extract.

Examples of the anti-ulcer agent include lansoprazole, omeprazole, rabeprazole, famotidine, cimetidine, and ranitidine hydrochloride. Examples of the antitussive expectorant drug include theophylline, potassium guiaiacolsulfonate, and guaifenesin. Examples of the antiemetic agent include metoclopramide. Examples of the bronchodilator include theophylline. Examples of the drug for allergy include amlexanox and seratrodast. Examples of the dental oral drug include oxytetracycline, and triamcinolone acetonide.

Examples of the cardiotonic agent include digoxin. Examples of the agent for arhythmia include pindolol. Examples of the diuretic drug include furosemide, and hydrochlorotiazide. Examples of the hypotensive agent include candesartan cilexetil, methyldopa, perindopril erbumine, and nifedipine.

Examples of the coronary vasodilator include molsidomine. Examples of the peripheral vasodilator include cinnarizine. Examples of the cholagogue include trepibutone. Examples of the antibiotic include cephem antibiotics such as cefadroxil, cefixime, cefditoren pivoxil, cefteram pivoxil, and cefpodoxime proxetil, synthetic antibiotics such as ampicillin, cyclasin, nalidixic acid, and enoxacin, monobactam antibiotics such as carumonam sodium, penem antibiotics and carbapenem antibiotics.

Examples of the chemotherapeutic include sulfamethizole. Examples of the agent for diabetes include tolbutamide, voglibose, glibenclamide, and troglitazone. Examples of the agent for osteoporosis include ipriflavone. Examples of the skeletal muscle relaxant include methocarbamol. Examples of the anticonvulsive agent include dimenhydrinate. Examples of the antirheumatic drug include methotrexate and bucillamine. Examples of the hormone agent include liothyronine sodium, dexamethazone sodium phosphate, prednisolone, oxendolone, and leuprorelin acetate. Examples of the alkaloid narcotic include opium, and ipecac. Examples of the sulfa agent include sulfisomidine, and sulfamethizole. Examples of the gout treating drug include allopinol, and colchicine. Examples of the blood coagulation arresting agent include dicoumarol. Examples of the anti-malignant tumor agent include 5-fluorouracil, uracil, and mitomycin.

Examples of the anti-obesity drug include trans-N-(4-((2S, 6R)-2,6-dimethylmorpholino) phenyl)-4-(tert-butylsulfonylamino) cyclohexanecarboxyamide, trans-N-(6-(5,6-dihydropyridin-1(2H)-yl) pyridin-3-yl)-4-(tert-butylsulfonylamino) cyclohexanecarboxyamide, trans-N-(6-(4trifluoromethyl) phenyl) pyridin-3-yl)-4-(tert-butylsulfonylamino) cyclohexanecarboxyamide, trans-N-(6-fluorobenzo [d]thiazol-2-yl)-4(tert-butylsulfonylamino) cyclohexanecarboxyamide, and following compounds.

[Formula 1]

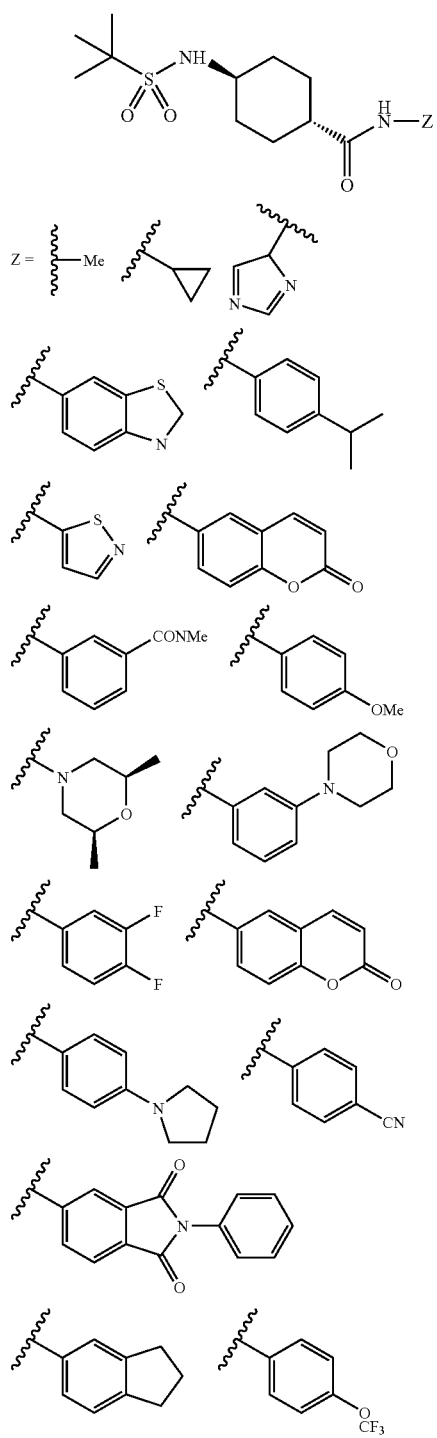

A content of the drug in the preparation of present invention is preferably a content at which an almost all amount of the drug can be dissolved out from the preparation and, specifically, is preferably 20 to 50% by weight, more preferably 25 to 50% by weight, further preferably 30 to 50% by weight. When a content is less than this amount, in the case of the same amount of the drug, an amount of a necessary additive is increased, and there is a possibility that the preparation becomes a preparation having such a big size that a patient takes the preparation with difficulty. When the content is more than this amount, there is a fear that solubility of the drug can not be sufficiently improved.

A content of nicotinic acid amide and/or urea in the preparation of present invention is preferably such that nicotinic acid amide and/or urea is 0.1 to 10% by weight, and the drug is 20 to 50% by weight, more preferably such that nicotinic acid amide and/or urea is 1 to 8% by weight, and the drug is 25 to 50% by weight, further preferably such that nicotinic acid amide and/or urea is 2 to 7% by weight, and the drug is 30 to 50% by weight.

The water-soluble polymer used in the present invention may be a water-soluble polymer used in the medical field. The water-soluble polymer is preferably one or two or more selected from polyvinylpyrrolidone, water-soluble cellulose, polyvinyl alcohol, polyvinyl acetate, gelatin, agar, sodium alginate, pectin, pullulan, gum xanthan, gum arabic, chondroitin sulfate, hyaluronic acid and carrageenan.

Among the water-soluble polymer used in the present invention, the water-soluble cellulose is one or two or more selected from hydroxypropylcellulose, hydroxypropylmethylcellulose, hydroxypropylmethylcellulose phthalate, hydroxypropylmethylcellulose acetate succinate and carboxymethylcellulose sodium.

Among the water-soluble polymer, more preferable is polyvinylpyrrolidone and/or hydroxypropylmethylcellulose acetate succinate.

A content of the water-soluble polymer in the preparation of present invention is preferably a content at which an almost all amount of the drug can be dissolved out from the preparation, and is preferably 40 to 79.9% by weight, more preferably 42 to 74% by weight, further preferably 43 to 68% by weight. When the content is less than this amount, since the crystal precipitation suppressing effect of the water-soluble polymer is decreased, there is a possibility that the drug is crystallized during a production process, an amorphous preparation is not obtained and, even if an amorphous preparation is obtained, the preparation is easily crystallized during storage, and solubility can be increased only for a short time and, when the content is more than this amount, there is a fear that solubility can not be improved.

A content of nicotinic acid amide and/or urea, the drug and the water-soluble polymer in the preparation of present invention is preferably such that nicotinic acid amide and/or urea is 0.1 to 10% by weight, the drug is 20 to 50% by weight, and the water-soluble polymer is 40 to 79.9% by weight, more preferably such that nicotinic acid amide and/or urea is 1 to 8% by weight, the drug is 25 to 50% by weight, and the water-soluble polymer is 42 to 74% by weight, further preferably such that nicotinic acid amide and/or urea is 2 to 7% by weight, the drug is 30 to 50% by weight, and the water-soluble polymer is 43 to 68% by weight.

A preferable combination of nicotinic acid amide and/or urea, and the water-soluble polymer is a combination of nicotinic acid amide and polyvinylpyrrolidone, a combination of nicotinic acid amide and hydroxypropylmethylcellulose acetate succinate, a combination of urea and polyvinylpyrrolidone, a combination of urea and hydroxypropylmethylcellulose acetate succinate, a combination of nicotinic acid amide, urea and polyvinylpyrrolidone, and a combination of nicotinic acid amide, urea and hydroxypropylmethylcellulose acetate succinate.

A preferable combination of particularly preferable nicotinic acid amide and/or urea, and the water-soluble polymer is a combination of polyvinylpyrrolidone and nicotinic acid amide, and a combination of hydroxypropylmethylcellulose acetate succinate, and urea.

Each content of a combination of polyvinylpyrrolidone, nicotinic acid amide and a drug (e.g. hypotensive agent) in the present preparation is preferably such that polyvinylpyrrolidone is 40 to 79.9% by weight, nicotinic acid amide is 0.1 to 10% by weight, and the drug is 20 to 50% by weight, more preferably such that polyvinylpyrrolidone is 42 to 74% by weight, nicotinic acid amide is 1 to 8% by weight, and the drug is 25 to 50% by weight, further preferably such that polyvinylpyrrolidone is 43 to 68% by weight, urea is 2 to 7% by weight, and the drug is 30 to 50% by weight.

Each content of a combination of hydroxypropylmethylcellulose acetate succinate, urea and the drug (e.g. anti-obesity drug) in the preparation of present invention is preferably such that hydroxypropylmethylcellulose acetate succinate is 40 to 79.9% by weight, urea is 0.1 to 10% by weight, and the drug is 20 to 50% by weight, more preferably such that hydroxypropylmethylcellulose acetate succinate is 42 to 74% by weight, urea is 1 to 8% by weight, and the drug is 25 to 50% by weight, further preferably such that hydroxypropylmethylcellulose acetate succinate is 43 to 68% by weight, urea is 2 to 7% by weight, and the drug is 30 to 50% by weight.

In the process for producing a preparation of the present invention, preferably, a powder obtained by mixing nicotinic acid amide and/or urea, the drug and the water-soluble polymer is dissolved in a solvent, the solvent is removed, and the resulting solid matter is ground to a suitable particle size. The solvent may be a solvent in which all of nicotinic acid amide and/or urea, the drug and the water-soluble polymer are dissolved therein. A specific solvent is water, alcohol, acetone, halogenated carbon and a mixture of the solvents. In addition, as a method of removing the solvent, there are a method of removing the solvent under warming and reduced pressure, and a method of drying and removing the solvent with a spray dryer.

It has been revealed that, in the present invention, upon formation of the solid dispersion, when an amount of nicotinic acid amide and urea in the solid dispersion is too large, solubility in water of the drug is reduced. Now, in the present invention, a content of nicotinic acid amide and urea in the preparation is optimized, and it was found out that solubility in water of the drug is increased. In addition, improvement in solubility in water of the drug was also performed by confirming the amorphous state by X-ray diffraction analysis.

The produced preparation of present invention is obtained in a form of a powder, a granule or a mass of a solid. Even when the present preparation is obtained in a form of a mass, a solid powder can be obtained by grinding. These obtained preparations of present invention may be contained in a granule or a tablet. As excipients, binders, lubricants or the like used in the granule or the tablet, those that have previously been used in pharmaceuticals can be used. For example, there are excipients such as lactose, sucrose, D-mannitol and the like, disintegrating agents such as croscarmellose sodium, partially gelatinized starch, carmellose calcium and the like, binders such as carmellose, carmellose sodium, hydroxypropylcellulose and the like, lubricants such as magnesium stearate and the like, and coating agents such as methacrylic acid copolymer, hydroxypropyolcellulose, hydroxypropylmethylcellulose and the like.

EXAMPLES

The present invention will be illustrated in more detail below by way of Production Examples, Examples and Comparative Examples, but the present invention is not limited by these Examples.

(Process for Producing Preparation)

Nifedipine (manufactured by Wako Pure Chemical Industries, Ltd., molecular weight: 346.34, hereinafter referred to as "NP" in some cases) as the poorly water soluble drug, polyvinylpyrrolidone K25 (manufactured by BASF, molecular weight: about 30000, hereinafter referred to as "PVP" in some cases) as the water-soluble polymer, urea (manufactured by Wako Pure Chemical Industries, Ltd., molecular weight: 60.06, hereinafter referred to as "Urea" in some cases) and nicotinic acid amide (manufactured by Yuki Gosei Kogyo Co, ltd., molecular weight: 122.13, hereinafter referred to as "NA" in some cases) were used. As shown in Table 1, nifedipine, polyvinylpyrrolidone, nicotinic acid amide and urea were mixed at a proportion, each mixture was dissolved in ethanol, the solvent was removed under warming at 40° C. and reduced pressure, and the resulting solid matter was ground into the powder state with a tablet grinding machine KC-HUK-type (manufactured by KONISHI).

(Method of Measuring Dissolution Rate)

The preparation powder having a nifedipine content corresponding to 100 mg was compression-molded at a pressure of 20 kN into a disc having a diameter of 2 cm. Using this disc, and employing distilled water (900 mL, 37° C.) as a test solution, a dissolution test was performed by the USP rotation disc method (100 rpm). A nifedipine concentration in the test solution was measured every one minutes with a solution monitoring device DM-3100 (manufactured by Otsuka Electronics Co., Ltd.) (detection wavelength: 350 nm, background measurement wavelength: 500 nm).

(Powder X-Ray Diffraction)

A powder X-ray diffraction pattern of the preparation was investigated using a powder X-ray diffraction device RINT2000 or RINTTTRIII (manufactured by Rigaku Corporation).

(Influence of Drug Content on Dissolution Property of Drug)

In order to observe influence of a drug content on the dissolution property of the drug, preparations (Reference Examples 1 to 3, Comparative Example 1) in which nicotinic acid amide or urea is not contained therein, and a content ratio of nifedipine (NP) and polyvinylpyrrolidone (PVP) 125 is 6/94, 10/90, 20/80, or 30/70 as shown in Table 1, were produced by the aforementioned process.

TABLE 1

|  | Reference Example 1 | Reference Example 2 | Reference Example 3 | Comparative Example 1 |
|---|---|---|---|---|
|  |  |  |  | (weight %) |
| Nifedipine | 6.0 | 10.0 | 20.0 | 30.0 |
| Polyvinylpyrrolidone | 94.0 | 90.0 | 80.0 | 70.0 |
| Total | 100.0 | 100.0 | 100.0 | 100.0 |

(Experimental Results)

Regarding these preparations, after conversion into amorphous was confirmed, a dissolution test was performed by the aforementioned method. As a result, as shown in FIG. 1, in any preparation, the halo pattern was observed in X-ray diffraction, and it was suggested that nifedipine was converted into amorphous. On the other hand, the dissolution property of nifedipine was investigated with time and, as a result, as shown in FIG. 2, in the preparation having a nifedipine content of up to 20%, nifedipine was rapidly dissolved supersaturated, but in the preparation having a nifedipine content of 30%, crystallization of the drug on a surface of the preparation was occurred, and nifedipine was only dissolved to an extent of solubility (about 6 μg/mL) of nifedipine although amorphous.

(Influence of Nicotinic Acid Amide on Dissolution Property of Drug)

As shown in Table 2, a preparation containing nicotinic acid amide and 30% of nifedipine was produced, conversion into amorphous was confirmed, and dissolution behavior was investigated.

TABLE 2

|  | Example 1 | Example 2 | Example 3 | Example 4 |
|---|---|---|---|---|
|  |  |  |  | (weight %) |
| Nifedipine | 30.0 | 30.0 | 30.0 | 30.0 |
| Polyvinylpyrrolidone | 69.5 | 69.0 | 68.0 | 66.5 |
| Nicotinic acid amide | 0.5 | 1.0 | 2.0 | 3.5 |
| Total | 100.0 | 100.0 | 100.0 | 100.0 |

|  | Example 5 | Comparative Example 1 | Comparative Example 2 |
|---|---|---|---|
|  |  |  | (weight %) |
| Nifedipine | 30.0 | 30.0 | 30.0 |
| Polyvinylpyrrolidone | 63.0 | 70.0 | 56.0 |
| Nicotinic acid amide | 7.0 | — | 14.0 |
| Total | 100.0 | 100.0 | 100.0 |

(Experimental Results)

Regarding these preparations, after conversion into amorphous was confirmed, a dissolution test was performed by the aforementioned method. As a result, as shown in FIG. 3, in any preparation, the halo pattern was observed in X-ray diffraction, and it was suggested that nifedipine was converted into amorphous. On the other hand, the dissolution concentration of nifedipine was investigated with time and, as a result, as shown in FIG. 4, in the preparations having a nicotinic acid amide content of 2 to 7% by weight (Examples 3 to 5), the drug in the preparation was dissolved at 90% or more at maximum and, in the preparations having a nicotinic acid amide content of 0.5 to 1% by weight (Examples 1 to 2), the drug in the preparation was dissolved out at 70% or more at maximum, and thus, the dissolution property was greatly improved as compared with the preparation (Comparative Example 1) not containing nicotinic acid amide. To the contrary, in the preparation (Comparative Example 2) having a nicotinic acid amide content of 14% by weight, the dissolution property improving effect was observed, but a maximum dissolution concentration of nifedipine was reduced as compared with the preparation having a nicotinic acid amide content of 0.5 to 7% by weight.

(Influence of Urea on Dissolution Property of Drug)

As shown in Table 3, a preparation containing urea, and 30% by weight of nifedipine was produced, conversion into amorphous was confirmed, and dissolution behavior was investigated.

TABLE 3

|  | Example 6 | Comparative Example 1 |
|---|---|---|
|  |  | (weight %) |
| Nifedipine | 30.0 | 30.0 |
| Polyvinylpyrrolidone | 63.0 | 70.0 |
| urea | 7.0 | — |
| Total | 100.0 | 100.0 |

(Experimental Results)

Regarding these preparations, after conversion into amorphous was confirmed, a dissolution test was performed by the aforementioned method. As a result, as shown in FIG. 5, in any preparation, the halo pattern was observed in X-ray diffraction, and it was suggested that nifedipine was converted into amorphous. On the other hand, the dissolution property of nifedipine was investigated with time and, as a result, as shown in FIG. 6, in the preparation (Example 6) containing urea, the dissolution property was greatly improved as compared with the preparation (Comparative Example 1) not containing urea.

INDUSTRIAL APPLICABILITY

Even for a drug having a high content of the drug and having very low solubility of the drug, it has become possible to improve the dissolution property of the drug by preparation of present invention.

The invention claimed is:

1. A solid preparation comprising 20 to 50% by weight of a drug, 0.1 to 10% by weight of nicotinic acid amide and/or urea, and a water-soluble polymer.

2. The solid preparation according to claim 1, wherein the content of nicotinic acid amide and/or urea is 2 to 7% by weight.

3. The solid preparation according to claim 1, wherein solubility in water of the drug is not more than 100 µg/mL.

4. The solid preparation according to claim 1, wherein the water-soluble polymer is one or more selected from the group consisting of polyvinylpyrrolidone, water-soluble cellulose, polyvinyl alcohol, polyvinyl acetate, gelatin, agar, sodium alginate, pectin, pullulan, gum xanthan, gum arabic, chondroitin sulfate, hyaluronic acid and carrageenan.

5. The solid preparation according to claim 4, wherein the water-soluble cellulose is one or more selected from the group consisting of hydroxypropylcellulose, hydroxypropylmethylcellulose, hydroxypropylmethylcellulose phthalate, hydroxypropylmethylcellulose acetate succinate and carboxymethylcellulose sodium.

6. The solid preparation according to claim 4, wherein the water-soluble polymer is polyvinylpyrrolidone and/or hydroxypropylmethylcellulose acetate succinate.

7. A method for improving solubility of a drug comprising preparing a solid composition comprising 20 to 50% by weight of the drug, 0.1 to 10% by weight of nicotinic acid amide and/or urea, and a water-soluble polymer.

8. The solid preparation according to claim 1, wherein the water-soluble polymer is polyvinylpyrrolidone.

9. The solid preparation according to claim 2, wherein the water-soluble polymer is polyvinylpyrrolidone.

10. A solid preparation comprising about 30% by weight of a drug, 63 to 68% by weight of a water-soluble polymer, and 2 to 7% by weight of nicotinic acid amide.

11. The solid preparation according to claim 10, wherein the water-soluble polymer is polyvinylpyrrolidone.

12. The solid preparation according to claim 1 that comprises nicotinic acid amide.

13. The solid preparation according to claim 8 that comprises nicotinic acid amide.

* * * * *